United States Patent [19]

Rüger et al.

[11] Patent Number: 4,918,073

[45] Date of Patent: Apr. 17, 1990

[54] DIARYLALKYL-SUBSTITUTED ALKYLAMINES AND MEDICAMENTS CONTAINING THEM

[75] Inventors: Wolfgang Rüger, Kelkheim; Hansjörg Urbach, Kronberg; Wilhelm Bartmann, Bad Soden am Taunus; Joachim Kaiser, Frankfurt am Main, all of Fed. Rep. of Germany

[73] Assignee: Hoechst Aktiengesellschaft, Fed. Rep. of Germany

[21] Appl. No.: 1,204

[22] Filed: Jan. 7, 1987

[30] Foreign Application Priority Data

Jan. 9, 1986 [DE] Fed. Rep. of Germany ....... 3600390

[51] Int. Cl.⁴ .................. A61K 31/495; C07D 241/04
[52] U.S. Cl. ..................................... 514/255; 540/575; 544/363; 544/389; 544/390; 544/391; 544/396; 544/397; 544/398; 546/139; 546/149; 546/192; 546/223
[58] Field of Search ............... 544/389, 390, 391, 396; 514/255

[56] References Cited

U.S. PATENT DOCUMENTS 3,239,528  3/1966  von Bebenberg et al. ....... 544/290
4,112,091  9/1978  Nesvadba et al. ................. 544/389
4,265,894  5/1981  Gootjes ............................. 544/391

OTHER PUBLICATIONS

Henning, et al., "Chemical Abstracts", vol. 106, 1987, Col. 106:196273r.

Lerch, et al., "Chemical Abstracts", vol. 107, 1987, Col. 107:23230s.

Rueger, et al., "Chemical Abstracts", vol. 107, 1987, Col. 107:236737z.

Primary Examiner—Richard L. Raymond
Assistant Examiner—James H. Turnipseed
Attorney, Agent, or Firm—Finnegan, Henderson, Farabow, Garrett and Dunner

[57] ABSTRACT

A compound I

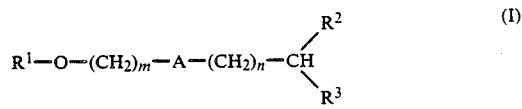

in which $R^1$ is cycloalkyl, alkenyl, cycloalkenyl, phenyl,

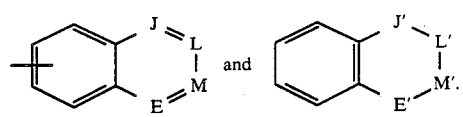

where
J, L, M, and E are methine or nitrogen and J', L', M', and E' are methylene, carbonyl or imino;
$R^2$ is phenyl or phenylalkyl;
a is various amine radicals;
m is 2, 3 or 4; and
n is 1, 2, 3, or 4 is described; salts of these compounds I are also described. Compounds I and the salts are calcium antagonists.

5 Claims, No Drawings

DIARYLALKYL-SUBSTITUTED ALKYLAMINES AND MEDICAMENTS CONTAINING THEM

The invention relates to diarylalkyl-substituted alkylamines, processes for their preparation, their use as medicines and medicaments containing them, and intermediate products for their preparation.

Numerous diarylbutylpiperidine and diarylbutylpiperazine derivatives are used therapeutically as neuroleptics on the basis of their action as antagonists of dopamine. Structurally related compounds from the series of benzhydrylpiperazine and diarylbutylpiperazine derivatives, such as, for example, cinnarizine, flunarizine and lidoflazine, act as inhibitors of the inflow of calcium ions into cells. They are used as therapeutics for the treatment of cardiovascular and cerebrovascular diseases.

N-Arylpiperazine-alkane-amides with diarylbutyl substituents on the piperazine systems are described in European Patent Application 68,544: they improve the circulation of the heart and protect it from the consequences of ischemia, anoxia or hypoxia.

N-(ω-Alkoxyalkyl)-3- and -4-benzhydrylpiperidines which are used as inhibitors of gastric acid secretion are known from U.S. Pat. No. 3,634,432. They differ from the compounds according to the invention by the substituent on the etherified hydroxyl group $X_1$ (see Examples 12 and 13), which can be lower alkyl, aralkyl or 2-tetra-hydropyranyl (see column 2, lines 19-23) but can in no case have the meaning of the corresponding substituent $R^1$ according to the invention. Neither is a calcium-antagonistic action assumed.

Spanish Pat. No. 504,202 describes benzhydryl-piperazine derivatives in which, however, the benzhydryl group is always bonded directly, and not by a $(CH_2)_n$ bridge, to one nitrogen of the piperazine. Moreover, these compounds show only a vasodilating action and not a calcium-antagonistic action.

It was suprising that the compounds of the present invention inhibit the inflow of calcium ions into cells to an unusually high degree. They are thus suitable as therapeutics for the treatment of various diseases, in particular of the cardiovascular system and of the cerebral vessels.

The present invention relates to compounds of the formula I $$R^1-O-(CH_2)_m-A-(CH_2)_n-CH\begin{matrix}R^2\\ \\R^3\end{matrix} \quad (I)$$

which have an outstanding calcium-antagonistic action and in which:

$R^1$ denotes $(C_3-C_8)$-cycloalkyl, straight-chain or branched $(C_2-C_6)$-alkenyl, $(C_5-C_8)$-cycloalkenyl,

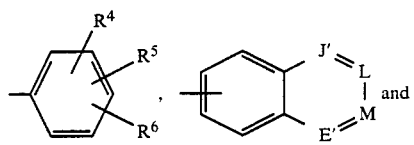

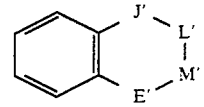

in which $R^4$, $R^5$ and $R^6$ are identical or different and independently of one another denote hydrogen, $(C_1-C_6)$-alkyl, $(C_3-C_8)$-cycloalkyl, hydroxyl, $(C_1-C_4)$-alkoxy, $(C_1-C_4)$-alkylthio, F, Cl, Br, I, nitro, cyano, trifluoromethyl, formyl, carboxyl, $(C_1-C_6)$-alkoxycarbonyl, $(C_1-C_6)$-acyl, carbamoyl, N,N-mono- or di-$(C_1-C_6)$-alkylcarbamoyl, sulfo, $(C_1-C_6)$-alkoxysulfonyl, sulfamoyl, N-mono- or N,N-di-$(C_1-C_6)$-alkylsulfamoyl, $(C_1-C_6)$-alkylsulfinyl, $(C_1-C_6)$-alkylsulfonyl or amino, unsubstituted or substituted by one or two identical or different $(C_1-C_6)$-alkyl, $(C_1-C_6)$-acyl or aryl, preferably phenyl, groups, J, L, M and E are identical or different and independently of one another denote methine or nitrogen J', L', M' and E' are identical or different and independently of one another denote methylene, carbonyl or imino, unsubstituted or substituted on the nitrogen by $(C_1-C_6)$-alkyl, $(C_1-C_6)$-acyl or aryl, preferably phenyl, $R^2$ and $R^3$ are identical or different and independently of one another denote phenyl or phenyl-$(C_1-C_4)$-alkyl, the phenyl ring in each case being unsubstituted or substituted by one, two or three substituents from the group comprising $(C_1-C_4)$-alkyl, $(C_1-C_4)$-alkoxy, F, Cl, Br, I, cyano, nitro and trifluoromethyl, and A denotes an amine

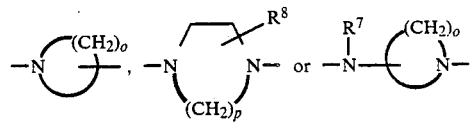

in which $R^7$ denotes hydrogen, $(C_1-C_6)$-alkyl or aryl, preferably phenyl, $R^8$ denotes hydrogen, $(C_1-C_6)$-alkyl, formyl, $(C_1-C_6)$-acyl, carboxyl, $(C_1-C_6)$-alkoxycarbonyl, carbamoyl or N-mono- or N,N-di-$(C_1-C_6)$-alkylcarbamoyl, o denotes 3, 4, 5, 6 or 7, p denotes 2 or 3, m denotes 2, 3 or 4 and n denotes 1, 2, 3 or 4, and the salts of the compounds of the formula I with physiologically acceptable acids.

Preferred compounds of the formula I are those in which at least one of the radicals and indices has the following meaning:

$R^1$ denotes $(C_3-C_8)$-cycloalkyl,

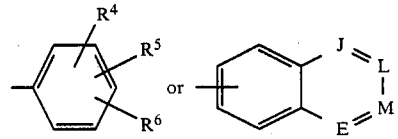

in which $R^4$ and $R^5$ are identical or different and independently of one another denote hydrogen, $(C_1-C_6)$-alkyl, $(C_1-C_4)$-alkoxy, F, Cl, Br, I, nitro, cyano, trifluoromethyl, formyl, carboxyl, $(C_1-C_6)$-alkoxycarbonyl, ($C_1$–$C_6$)-acyl, carbamoyl, N-mono- or N,N-di-($C_1$–$C_6$)-alkylcarbamoyl, sulfo, ($C_1$–$C_6$)-alkoxysulfonyl, sulfamoyl, N-mono- or N,N-di-($C_1$–$C_6$)-alkylsulfamoyl, ($C_1$–$C_6$)-alkylsulfinyl or ($C_1$–$C_6$)-alkylsulfonyl, $R^6$ denotes hydrogen and J, L, M and E are identical or different and independently of one another denote methine or nitrogen, $R^2$ and $R^3$ are identical or different and independently of one another denote phenyl, which is unsubstituted or substituted by one, two or three substituents from the group comprising methyl, ethyl, methoxy, ethoxy, F, Cl, Br, I, cyano, nitro and trifluoromethyl, and A denotes an amine

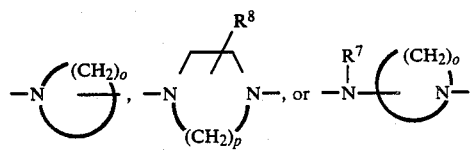

in which $R^7$ denotes hydrogen, methyl or ethyl, $R^8$ denotes hydrogen, carboxyl or carbamoyl, o denotes 4, 5 or 6, and p denotes 2 or 3, m denotes 2, 3 or 4 and n denotes 1, 2, 3 or 4, and the salts of the compounds of the formula I with physiologically acceptable acids.

Particularly preferred compounds of the formula I are those in which at least one of the substituents and indices has the following meaning:

$R^1$ denotes ($C_5$–$C_7$)-cycloalkyl,

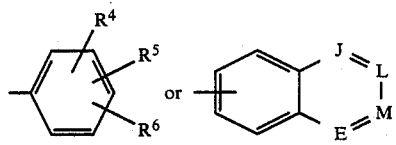

in which $R^4$ denotes hydrogen, methyl, ethyl, propyl, isopropyl, n-butyl, s-butyl, isobutyl, tert. butyl, methoxy, ethoxy, fluorine, chlorine, bromine, nitro, cyano or trifluoromethyl, $R^5$ and $R^6$ denote hydrogen and J, L, M and E are identical or different and independently of one another denote methine or nitrogen, $R^2$ and $R^3$ are identical or different and independently of one another denote phenyl, which is unsubstituted or substituted by one, two or three substituents from the group comprising methyl, fluorine, chlorine, bromine, cyano, nitro and trifluoromethyl, A denotes an amine

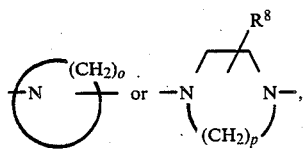

in which $R^8$ denotes hydrogen, carboxyl or carbamoyl, o denotes 4, 5 or 6 and p denotes 2 or 3, m denotes 2, 3 or 4 and n denotes 2, 3 or 4, and the salts of the compounds of the formula I with physiologically acceptable acids.

Especially preferred compounds of the formula I are those in which at least one of the substituents or indices has the following meaning:

$R^1$ denotes cyclohexyl, phenyl, which is unsubstituted or substituted by methyl, tert. butyl, methoxy, fluorine, nitro, cyano or trifluoromethyl, or denotes naphthyl, quinolinyl or isoquinolinyl, $R^2$ and $R^3$ are identical or different and independently of one another denote phenyl, which is unsubstituted or substituted by fluorine or trifluoromethyl, A denotes an amine

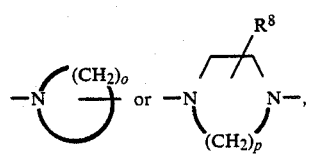

in which $R^8$ denotes hydrogen, o denotes 5 and p denotes 2, m denotes 2 and n denotes 3, and the salts of the compounds of the formula I with physiologically acceptable acids.

Possible acids of this type are inorganic acids, such as hydrochloric acid, hydrobromic acid, hydriodic acid, sulfuric acid, phosphoric acid or nitric acid, or organic acids, such as tartaric acid, citric acid, malic acid, lactic acid, maleic acid, fumaric acid, malonic acid, oxalic acid, acetic acid, propionic acid, methanesulfonic acid, benzenesulfonic acid, p-toluenesulfonic acid, naphthalene-1,5-disulfonic acid or gluconic acid.

The compounds of the formula I in some cases have asymmetric carbon atoms and can therefore occur as enantiomers and diastereomers. The invention relates both to the pure enantiomers and to the racemates. The racemates can be resolved into the enantiomers by customary methods, for example by salt formation with optically active acids, such as camphorsulfonic acid or dibenzoyltartaric acid, fractional crystallization and subsequent liberation of the bases from their salts, or by derivatization with suitable optically active reagents, resolution of the diastereomeric derivatives by fractional crystallization or chromatography on silica gel or aluminum oxide, and cleavage again. Then diastereomers can be resolved by customary methods, such as fractional crystallization or chromatography on columns.

The present invention furthermore relates to a process for the preparation of compounds of the formula I, which comprises (a) reacting a compound of the formula II $$R^1\text{—O—}(CH_2)_m\text{—Q} \qquad (II)$$

in which $R^1$ and m have the same meaning as in formula I and in which Q denotes a leaving group which can be displaced nucleophilically, in particular a Cl, Br or I atom or a sulfonic acid radical, preferably a methanesulfonyl, benzenesulfonyl, p-toluenesulfonyl or trifluoromethanesulfonyl radical, with a compound of the formula III

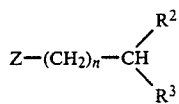 (III)

in which $R^2$, $R^3$ and n have the same meaning as in formula I and in which Z denotes

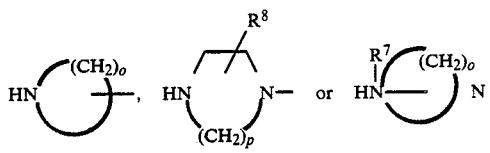

in which
$R^7$, $R^8$, o and p have the same meaning as in formula I, under the conditions of nucleophilic replacement, preferably in a polar organic solvent, such as an alcohol, preferably methanol, ethanol, propanol or isopropanol, or a lower ketone, preferably acetone, methyl ethyl ketone or methyl isobutyl ketone, or in acetonitrile, dimethylformamide, dimethyl sulfoxide or sulfolane, or a hydrocarbon, preferably toluene, in the presence or absence of an auxiliary base for trapping the acid which forms, preferably in the presence of potassium carbonate, sodium carbonate, triethylamine, pyridine, 1,5-diazabicyclo[5,4,0]undec-5-ene or 1,5-diazabicyclo-[4,3,0]non-5-ene, and in the presence or absence of an alkali metal halide, preferably sodium iodide or potassium iodide, at a temperature between 0° and 160° C., preferably between 20° and 120° C., or which comprises (b) reacting a compound of the formula IV

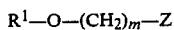 (IV)

in which $R^1$ and m have the same meaning as in formula I and Z has the same meaning as in formula III, with a compound of the formula V

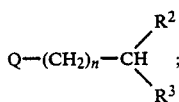 (V)

in which $R^2$, $R^3$ and n have the same meaning as in formula I and Q has the same meaning as in formula II, under the conditions of nucleophilic replacement as described under (a), or which comprises (c) reacting a compound of the formula VI

 (VI)

in which $R^1$ has the same meaning as in formula I, with a compound of the formula VII

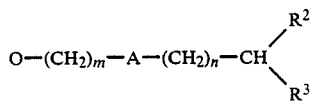 (VII)

in which $R^2$, $R^3$, A, m and n have the same meaning as in formula I and Q has the same meaning as in formula II, either in a polar aprotic solvent, such as acetonitrile, tetrahydrofuran, dimethyl sulfoxide, dimethylformamide, sulfolane or N-methylpyrrolidone, in the presence of a strong base, such as sodium hydride, potassium hydride, sodium amide, lithium diisopropylamide, butyllithium or lithium hexamethyldisilazide, preferably in dimethylformamide or dimethyl sulfoxide in the presence of sodium hydride or sodium amide, at a temperature between −40° and +100° C., preferably between −20° and +50° C., or in a protic or aprotic polar organic solvent, such as a lower alcohol, for example methanol, ethanol or isopropanol, or a lower ketone, preferably acetone, methyl ethyl ketone or methyl isobutyl ketone, or in dimethylformamide, in the presence of a weak to moderate-strength base, such as an alkali metal or alkaline earth metal hydroxide or carbonate, preferably sodium carbonate or potassium carbonate, or an amine, such as, for example, triethylamine, pyridine, N-ethyldiisopropylamine, 1,5-diazabicyclo-[5,4,0]undec-5-ene or 1,5-diazabicyclo-[4,3,0]non-5-ene, at a temperature between 0° and 160° C., preferably between 20° and 120° C., or which comprises (d) reacting a compound of the formula XIII

 (XIII), in which $R^1$ has the same meaning as in formula I and in which T denotes a leaving group which can be displaced nucleophilically, in particular a fluorine, chlorine, bromine or iodine atom, a nitro, hydroxyl, alkoxy or trialkylamminio group or a sulfonic acid radical, preferably a fluorine or chlorine atom, a nitro group or a methanesulfonyl, benzenesulfonyl, p-toluenesulfonyl or trifluoromethanesulfonyl radical, with a compound of the formula XIV

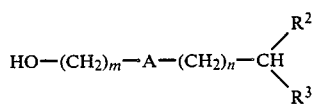 (XIV)

in which $R^2$, $R^3$, A, m and n have the same meaning as in formula I, under the conditions of nucleophilic replacement, for example without a solvent or in an aqueous solvent, preferably in a polar organic solvent, such as an alcohol, preferably methanol, ethanol, propanol or isopropanol, or a ketone, preferably acetone, methyl ethyl ketone, or methyl isobutyl ketone, or an ether, preferably diethyl ether, tert.-butyl methyl ether, dimethoxyethane, tetrahydrofuran or dioxane, or a halogenated hydrocarbon, preferably methylene chloride, chloroform or 1,2-dichloroethane, or in acetonitrile, dimethylformamide, dimethylsulfoxide or sulfolane, or in a hydrocarbon, preferably benzene or toluene, or in a mixed aqueous-organic solvent system, with the addition of a phase transfer catalyst, in the presence or absense of an auxiliary base for trapping the acid which forms, preferably in the presence of potassium carbonate, sodium carbonate, triethylamine, pyridine, lithium diisopropylamide, n-butyllithium, sodium hydride, potassium hydride, sodium amide, 1,5-diazabicyclo-[5.4.0]undec-5-ene or 1,5-diazabicyclo[4.3.0]-non-5-ene and in the presence or absence of copper powder, at a temperature between −80° and +200° C., preferably between −30° and +120° C.

The compounds of the formula II are known from the literature or can be prepared under analogous conditions from compounds of the formula VI by reaction with α,ω-dihalogenoalkanes or ω-halogenoalkylsulfonates.

The compounds of the formula III where Z is

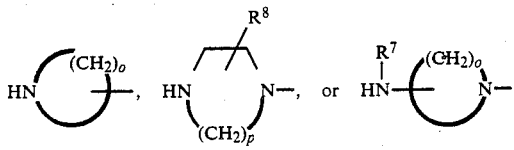

in which $R^7$, $R^8$, o and p have the same meaning as in formula I, can be prepared in a manner which is known per se from compounds of the formula VIII

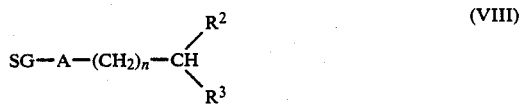

in which
$R^2$, $R^3$, A and n have the same meaning as in formula I and in which SG denotes a suitable protective group, such as, for example, a carbamate, amide, alkyl or benzyl group, preferably a formyl, ethoxycarbonyl, benzyl or trityl group, by splitting off the protective group under conditions which are known from the literature, for example under acid or alkaline cleavage or by hydrogenolysis.

The compounds of the formula III where Z is

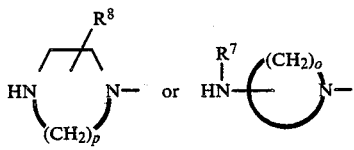

in which $R^7$, $R^8$, o and p have the same meaning as in formula I, can also be prepared by reaction of compounds of the formula V with amines of the formula Z-H, in which Z is one of the abovementioned groups, under the conditions of nucleophilic replacement, such as are described under process variant (a), or by reaction of compounds of the formula V with protected amines

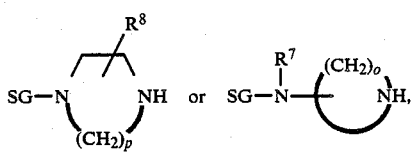

in which $R^7$, $R^8$, o and p have the same meaning as in formula I and SG has the same meaning as in formula VIII, under the conditions of nucleophilic replacement, such as are described under process variant (a), with subsequent splitting off of the protective group under customary conditions, for example by acid or alkaline cleavage or by hydrogenolysis.

The invention likewise relates to compounds of the formula III

in which:

$R^2$ and $R^3$ are identical or different and independently of one another denote phenyl or phenyl-($C_1$-$C_4$)-alkyl, the phenyl ring in each case being unsubstituted or substituted by one, two or three substituents from the group comprising ($C_1$-$C_4$)-alkyl, ($C_1$-$C_4$)-alkoxy, F, Cl, Br, I, cyano, nitro and trifluoromethyl, Z denotes

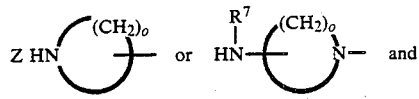

n denotes 1, 2, 3 or 4, but with the exception of the compound in which, at the same time, $R^2 = R^3 =$ phenyl, n=1 and

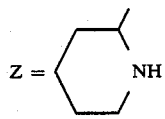

The compounds of the formula III in which Z is

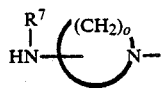

in which o has the same meaning as in formula I and $R^7$ is methyl, can preferably be prepared from compounds of the same formula, in which $R^7$ denotes an alkoxycarbonyl radical, by reduction with suitable reducing agents, preferably lithiumaluminum hydride.

The compounds of the formula IV can be prepared from the compounds of the formula II by processes analogous to those which have already been described for the preparation of the compounds of the formula III from the compounds of the formula V, or can be prepared from compounds of the formula IX $$R^1-O-(CH_2)_m-A-SG \quad (IX)$$

in which
$R^1$, A and m have the same meaning as in formula I and
SG has the same meaning as in formula VIII, by splitting off the protective group under customary conditions, for example by acid or alkaline cleavage or by hydrogenolysis, or from compounds of the formula VI by reaction with compounds of the formula X $$Q-(CH_2)_m-A-SG \quad (X)$$

in which
A and m have the same meaning as in formula I,
Q has the same meaning as in formula II and
SG has the same meaning as in formula VIII, under the conditions of an alkylation reaction, such as are described under process variant (c), followed by splitting off of the protective group under the customary conditions.

The compounds of the formula V are known from the literature in most cases or can be prepared in an analogous manner.

The compounds of the formula VI are known from the literature and in most cases are commercially available.

The invention furthermore relates to the compounds of the formula VII

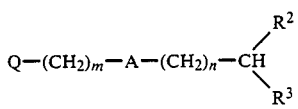   VII in which:

R[2] and R[3] are identical or different and independently of one another denote phenyl or phenyl-$(C_1-C_4)$-alkyl, the phenyl ring in each case being unsubstituted or substituted by one, two or three substituents from the group comprising $(C_1-C_4)$-alkyl, $(C_1-C_4)$-alkoxy, F, Cl, Br, I, cyano, nitro and trifluoromethyl, n denotes 1, 2, 3 or 4, A denotes an amine

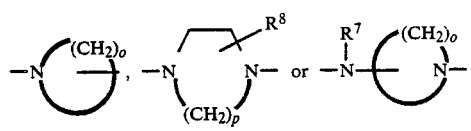

in which

R[7] denotes hydrogen, $(C_1-C_6)$-alkyl or aryl, preferably phenyl,

R[8] denotes hydrogen, $(C_1-C_6)$-alkyl, formyl, $(C_1-C_6)$-acyl, carboxyl, $(C_1-C_6)$-alkoxycarbonyl, carbamoyl or N-mono- or N,N-di-$(C_1-C_6)$-alkylcarbamoyl, o denotes 3, 4, 5, 6 or 7, p denotes 2 or 3, m denotes 2, 3 or 4 and Q denotes a leaving group which can be displaced nucleophilically, but with the exception of the compound in which, at the same time, R[2]=R[3]=4-fluorophenyl, n=3

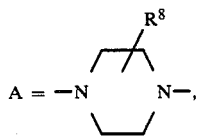

where R[8]=H, m=2 and

Q=Cl, and with the exception of the compound in which, at the same time, R[2]=R[3]=phenyl, n=1, A=

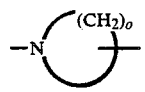

where o=5, m=2 and Q=Cl.

The compounds of the formula VII can be prepared from the compounds of the formula III by reaction with α,ω-dihalogenoalkanes or ω-halogenoalkylsulfonates under the conditions of nucleophilic replacement, such as are described under process variant (a), or from the compounds of the formula V by reaction with a compound of the formula XI

   (XI)

in which m has the same meaning as in formula I,

Q has the same meaning as in formula II and

Z has the same meaning as in formula III, under the conditions of nucleophilic replacement, such as are described under process variant (a), or from the compounds of the formula V by reaction with a compound of the formula XII $$HO-(CH_2)_m-Z \qquad (XII)$$

in which m has the same meaning as in formula I and

Z has the same meaning as in formula III, under the conditions of nucleophilic replacement, such as are described under process variant (a), to give compounds of the formula XIV, and subsequent conversion of the hydroxyl function into the leaving group Q by customary methods.

The compounds of the formula VIII are prepared from the compounds of the formula III with the aid of general processes of protective group chemistry, or from the compounds of the formula V by reaction with protected amines, as has already been described in the preparation of compounds of the formula III from those of the formula V.

The compounds of the formula IX are prepared from the compounds of the formula IV with the aid of general processes of protective group chemistry, or from the compounds of the formula VI by reaction with compounds of the formula X, as has already been described in the preparation of compounds of the formula IV from those of the formula VI.

The compounds of the formulae X, XI and XII are known or are accessible from commercially available starting materials by simple processes.

The compounds of the formula I according to the invention have biological actions, in particular calcium-antagonistic actions, and therefore have useful properties for the treatment of all disease conditions based on a disturbance in the calcium balance: in particular, they are suitable as hypotensive agents, antianginal agents and agents for improving cerebro-vascular circulation.

Their calcium-antagonistic activity can be demonstrated in the biochemical test model of displacement of tritium-labeled nitrendipine. This test was carried out in a membrane preparation obtained from the cortex of the rat brain and washed several times, the method described by R. J. Gould et al. (Proc. Natl. Acad. Sci. U.S.A. 79, 3656 [1982]) essentially being used. The membrane solution diluted to 1:1,500 with TRIS buffer pH 7.4 (50 mM TRIS-HCl, 150 mM NaCl, 1.0 mM $CaCl_2$ and 0.001% by weight, based on the TRIS-HCl, of NaCl and $CaCl_2$ in the solution, of a neutral surface-active substance, such as, for example, Genapol ®) was incubated in 5 ml portions with $^3$H-nitrendipine (0.1 nM in the test, specific activity 81.3 Ci/mmol) and with various concentrations of the test substances at 25° C. in a shaken waterbath for 60 minutes. The membrane fractions were separated off by vacuum filtration over Whatman-GF/F glass fiber filters and the radioactivity was measured in a liquid scintillation counter. The non-specific $^3$H-nitrendipine binding was determined in the presence of 1 μM nifedipine. The $IC_{50}$ value, i.e. the concentration of test substance which is capable of displacing 50% of the radioactively labeled nitrendipine, is determined as the characteristic parameter.

In this model, the compounds of the formula I according to the invention have $IC_{50}$ values of about $10^{-6}$ molar to about $10^{-9}$ molar. They thus have a clearly more powerful action than the known comparison compounds, such as flunarizine and lidoflazine.

The following table contains some of the $IC_{50}$ values measured.

| Example No. | $IC_{50}(10^{-9} M)$ | Example No. | $IC_{50}(10^{-9} M)$ |
|---|---|---|---|
| 16 | 22 | 61 | 60 |
| 17 | 12 | 64 | 19 |
| 18 | 48 | 66 | 12 |
| 22 | 85 | 68 | 0,9 |
| 28 | 65 | 69 | 2 |
| 32 | 12 | 71 | 4,2 |
| 36 | 90 | 73 | 1,2 |
| 37 | 400 | 74 | 1,0 |
| 41 | 8,5 | 75 | 9 |
| 45 | 11 | 81 | 3,6 |
| 50 | 4 | 83 | 70 |
| 56 | 180 | Flunarizine | 1000 |
|  |  | Lidoflazine | 430 |

The antianginal efficacy of the compounds according to the invention can be demonstrated in the pharmacological test model of coronary circulation on the isolated guineapig heart. For this test, female heparinized (2.5 mg of heparin sodium intraperitoneally 1 hour before sacrifice) guineapigs (220-250 g) were sacrificed by a blow on the neck. Immediately after the thorax has been opened, cardiac arrest was induced by cooling the heart with icecold saline solution. The ascending aorta was catheterized and connected to a non-recirculating perfusion system (hydrostatic pressure 65 cm of $H_2O$) in accordance with the method of Langendorff. Exposure of the heart was folowed by a perfusion period of 30 minutes for adaptation of the heart to the isolated state. A modified Krebs-Henseleit bicarbonate solution (113.8 mM NaCl, 22.0 mM $NaHCO_3$, 4.7 mM KCl, 1.2 mM $KH_2PO_4$, 1.1 mM $MgSO_4 \times 7$ $H_2O$ and 2.5 mM $CaCl_2 \times 2$ $H_2O$, equilibrated with 95% of $O_2$ and 5% of $CO_2$, pH 7.41, 38° C.) was used as the perfusate. Glucose (11 mM) and sodium pyruvate (2.0 mM) were added. The osmolality of the perfusate was kept constant by adjusting the amount of NaCl. The hearts were loaded with a resting voltage of 2 pond (p). The heart rate and contraction force were recorded isometrically and the equipment for this (Hellige GmbH, Freiburg, Germany) were calibrated to 2 p. The coronary flow was determined with the aid of a drop counter, 7 drops corresponding to 1 ml. The values stated are expressed as the percentage increase in coronary circulation after administration of the test substance in the stated dosage via a feed tube (0.1% strength solution in propanediol), based on control hearts without addition of the test substance. The following table contains some of the values measured:

| Example No. | Dose (μg) | Increase in coronary circulation in % (b) |
|---|---|---|
| 17 | 0.1 | 14-17 |
|  | 0.5 | 33-38 |
| 42 | 0.5 | 20-29 |
| 45 | 0.1 | 13-26 |
|  | 0.5 | 38-57 |
| 46 | 0.1 | 12-23 |
|  | 0.5 | 21-36 |
| 50 | 0.1 | 38 (a) |
| 56 | 1.0 | 40-65 |
| 62 | 0.1 | 9-13 |
| 67 | 0.1 | 5-21 |
|  | 0.5 | 23-35 |

-continued

| Example No. | Dose (μg) | Increase in coronary circulation in % (b) |
|---|---|---|
| 68 | 0.1 | 20-29 |
| 70 | 0.5 | 36-52 |

(a) mean value of 28 measurements
(b) the values stated result from in each case two measurements.

The compounds of the formula I likewise have a powerful action in other test models with which a calcium-antagonistic action can be demonstrated, for example by the relaxing action on the precontracted guinea-pig ileum or by the action potential of the isolated guinea-pig papillary muscle.

The compounds of the formula I according to the invention and their pharmacologically acceptable salts are active within a wide dose range. The level of dose administered depends on the nature of the desired treatment, on the mode of administration and on the condition, type and size of the patient treated. In the case of oral dosage, satisfactory results are achieved with doses from 0.01 mg, preferably from 0.1 mg and up to 100 mg, preferably up to 20 mg of a compound of the formula I per kg of body weight. On humans, the daily dose varies between 1 and 800 mg, preferably 2 and 500 mg, it being possible for individual doses of 0.5 to 200 mg to be administered, preferably once to three times daily. For intravenous and intramuscular use, the dose is 0.1 to 300 mg, preferably 0.5 to 150 mg daily.

The pharmacologically usable compounds of the present invention and their salts can be used for the preparation of pharmaceutical products which contain an active amount of the active substance together with excipients and which are suitable for enteral and parenteral administration. Tablets or gelatin capsules which contain the active compound together with diluents, for example lactose, dextrose, sucrose, mannitol, sorbitol, cellulose and/or glycine, and lubricants, such as silica, talc, stearic acid or salts thereof, such as magnesium or calcium stearate, and/or polyethylene glycol, are preferably used. Tablets also contain binders, such as magnesium aluminum silicate, starch, gelatin, tragacanth, methylcellulose, sodium carboxymethylcellulose and-/or polyvinylpyrrolidone and, if necessary, dyestuffs, flavor substances and sweeteners. Injectable solutions are preferably isotonic aqueous solutions or suspensions, which can be sterilized and can contain auxiliaries, such as preservatives, stabilizers, wetting agents and/or emulsifying agents, solubilizing agents, salts for regulating the osmotic pressure and/or buffer substances. The pharmaceutical products according to the invention which, if desired, can contain other pharmacologically useful substances, are prepared, for example, by means of conventional mixing, granulating and tablet-coating methods and contain 0.1% to about 75%, preferably about 1% to about 50% of the active compound.

The examples which follow are intended to illustrate the invention without limiting it to these examples.

A. Preparation of intermediate products

EXAMPLE 1

5-(2-chloroethoxy)isoquinoline hydrochloride

A solution of 29.2 g (0.2 mol) of 5-hydroxyisoquinoline in 300 ml of absolute dimethylformamide was added dropwise to 9.7 g of a 55-60% strength sodium hydride dispersion in 50 ml of absolute dimethylformamide so that the temperature rose to 45°–50° C., and the mixture was then subsequently stirred at room temperature for 2 hours. The resulting anion solution was then added dropwise to a solution of 49.5 g (0.21 mol) of chloroethyl p-toluene-sulfonate in 100 ml of absolute dimethylformamide and the mixture was subsequently stirred for 18 hours.

The solvent was evaporated off and the residue was partitioned between water and ethyl acetate. The organic phase was extracted with 2N HCl and the extract was brought to pH 10 with concentrated NaOH solution and extracted several times by shaking with methylene chloride. These extracts were dried and concentrated.

Yield: 34.8 g of yellow oil.

To prepare the hydrochloride, the crude product was dissolved in isopropanol and the solution was rendered acid with ethereal hydrochloric acid and cooled to 0° C. The precipitate which had separated out was filtered off with suction, washed with a little cold isopropanol and ether and dried.

Yield: 33.6 g; melting point 191°–194° C.

EXAMPLE 2

5-(3-chloropropoxy)isoquinoline hydrochloride

A solution of 20 g (0.138 mol) of 5-hydroxyisoquinoline in 200 ml of absolute dimethylformamide was added dropwise to 6.6 g of a 55–60% strength sodium hydride dispersion in 30 ml of absolute dimethylformamide so that the temperature was about 40° C., and the mixture was then subsequently stirred at room temperature for 1 hour. The resulting anion solution was then added dropwise to 65.2 g (0.414 mol) of 1-bromo-3-chloropropane and the mixture was stirred at 0° C. for 1 hour and at room temperature for 1 hour.

The solvent and excess bromochloropropane were stripped off under a high vacuum and the residue was partitioned between 2N NaOH and methylene chloride. The organic phase was washed twice more with water, dried and concentrated.

The hydrochloride was prepared as described under Example 1.

Yield: 28.1 g; melting point 186°–187° C.

The following compound was likewise prepared by an analogous procedure:

5-(4-chlorobutoxy)-isoquinoline hydrochloride, melting point 164°–167° C.

EXAMPLE 3

1-[4,4-bis(4-methoxyphenyl)butyl]piperazine (a) Bis(4-methoxyphenyl)cyclopropylcarbinol:

The Grignard reagent was prepared from 12.7 g (0.53 mol) of magnesium filings and 93.5 g (0.50 mol) of 4-bromoanisole in 160 ml of absolute ether. 26.0 g (0.228 mol) of ethyl cyclopropanecarboxylate were slowly added dropwise to this solution and the mixture was then heated at the reflux temperature for 2.5 hours. The reaction solution was poured onto ice and diluted with about 300 ml of saturated ammonium chloride solution, so that the resulting precipitate dissolved. The solution was then extracted with ether and the ethereal phase was washed with water, dried and concentrated. Vacuum distillation of the crude product gave 39.2 g of a fraction at 195°–200° C./0.18 mm Hg.

(b) 4-Bromo-1,1-bis(4-methoxyphenyl)butene:

165 ml of 48% strength HBr solution were added to 39.2 g (0.138 mol) of bis(4-methoxyphenyl)cyclopropylcarbinol and the mixture was stirred at 80° C. for 4.5 hours. After cooling, ether was added and the organic phase was separated off, washed with saturated NaHCO$_3$ solution and with water, dried and concentrated.

Yield: 44.0 g of a yellow oil.

NMR (CDCl$_3$, 60 MHz): δ=2.66 (t, 2H), 3.33 (t, 2H), 3.72 (s, 3H), 3.78 (s, 3H), 8.34 (t, 1H) and 6.6–7.2 (m, 8H) ppm.

(c) 4-Bromo-1,1-bis(4-methoxyphenyl)butane 44 g (0.127 mol) of 4-bromo-1,1-bis(4-methoxyphenyl)-butene were dissolved in 160 ml of ethanol, 2.8 g of palladium-on-charcoal (10%) were added and hydrogenation was carried out in a shaking vessel at room temperature in the course of about 2 hours. The catalyst was then filtered off with suction, the filtrate was concentrated and the crude product was purified by fractional distillation. 34.4 g of a fraction were obtained at 220°–226° C./−0.2 mm.

(d) 1-[4,4-Bis(4-methoxyphenyl)butyl]piperazine 14.0 g (0.04 mol) of 4-bromo-1,1-bis(4-methoxyphenyl)-butane, 8.2 g (0.052 mol) of ethyl piperazine-1-carboxylate, 11.04 g (0.08 mol) of powdered potassium carbonate and 0.6 g of potassium iodide were boiled under reflux in 160 ml of methyl isobutyl ketone for 30 hours. After cooling, the precipitate was filtered off with suction and the solvent was evaporated.

The material thus obtained was dissolved in 440 ml of ethanol, 440 ml of 4N KOH were added and the mixture was boiled under reflux for 26 hours. The ethanol was evaporated off, the aqueous phase which remained was extracted with methylene chloride, the extracts were extracted by shaking with 2N HCl and the acid phase was washed several times with ethyl acetate and then brought to pH 10 with concentrated NaOH and extracted with methylene chloride. The extracts were dried and concentrated.

Yield: 15.8 g.

NMR (CDCl$_3$, 60 MHz): δ=1.2–3.0 (m, 15H), 3.75 (s, 6H), 3.79 (t, 1H) and 6.6–7.2 (m, 8H) ppm.

The following were likewise prepared by an analogous procedure: 1-[4,4-bis(4-trifluoromethylphenyl)-butyl]-piperazine, NMR (CDCl$_3$, 60 MHz): δ=1.2–3.0 (m, 15H), 3.98 (t, 1H) and 7.1–7.6 (m, 8H) ppm; 1-(4,4-diphenyl-butyl)piperazine, melting point 58°–60° C., NMR (CDCl$_3$, 60 MHz): δ=1.2–3.0 (m, 15H), 3.85 (t, 1H) and 7.48 (s, 10H) ppm; 1-[4,4-bis(3-fluorophenyl)-butyl]piperazine, NMR (CDCl$_3$, 60 MHz): δ=1.2–3.0 (m, 14H), 3.85 (t, 1H), 4.60 (s, 1H) and 6.6–7.4 (m, 8H) ppm; 1-[4,4-bis(4-chlorophenyl)butyl]piperazine, melting point 28°–32° C.;

NMR (CDCl$_3$, 60 MHz): δ=1.1–3.0 (m, 15H), 3.80 (t, 1H) and 6.9–7.3 (m, 8H) ppm; and 1-[4,4-bis(4-fluorophenyl)-butyl]piperazine; melting point 77°–79° C.;

NMR (CDCl$_3$, 60 MHz), 1.2–3.0 (m, 15H), 3.83 (t, 1H) and 6.6–7.3 (m, 8H) ppm.

EXAMPLE 4

1-[3,3-bis(4-fluorophenyl)propyl]piperazine (a) Ethyl 2-cyano-3-(4-fluorophenyl)acrylate. 117.8 g (0.949 mol) of 4-fluorobenzaldehyde, 118.1 g (1.04 mol) of ethyl cyanoacetate and 2 ml of piperidine were dissolved in 500 ml of toluene, the solution was slowly heated to the reflux temperature and the water of reaction was removed using a water separator. After 30 minutes, the mixture was concentrated to about half the volume, the concentrate was cooled and the resulting precipitate was filtered off with suction. Yield: 171.5 g, melting point 96°–98° C.

(b) Ethyl 2-cyano-3,3-bis(4-fluorophenyl)propionate

A Grignard reagent was prepared from 6.82 g (0.281 mol) of magnesium filings and 48.1 g (0.275 mol) of 4-bromo-fluorobenzene in 150 ml of absolute ether. A solution of 54.8 g (0.250 mol) of ethyl 2-cyano-3-(4-fluorophenyl)-acrylate in 200 ml of toluene was added dropwise to this solution in the course of 10–15 minutes so that the temperature rose to about 90° C. and the ether was distilled off. Thereafter, the mixture was heated at the reflux temperature for a further 30 minutes and, after cooling, was poured onto 300 ml of ice and 15 ml of concentrated $H_2SO_4$, the aqueous phase was extracted once more with toluene and the combined organic phases were washed with water, dried and concentrated.

Yield: 79.1 g of yellow crystals.

Melting point 99°–101° C. (from isopropanol/n-hexane).

(c) 3,3-Bis(4-fluorophenyl)propionate 76.2 g (0.242 mol) of ethyl 2-cyano-3,3-bis(4-fluorophenyl)propionate were dissolved in 250 ml of hot glacial acetic acid, 250 ml of half-concentrated $H_2SO_4$ were added and the mixture was heated at the reflux temperature for 18 hours. Thereafter, the mixture was poured onto 1 kg of ice and extracted several times with ether and the extracts were washed with water, dried and concentrated.

Yield: 60.3 g of a yellow oil which gradually crystallized.

Melting point 97°–99° C. (from cyclohexane).

(d) 3,3-Bis(4-fluorophenyl)propanol 57.9 g (0.221 mol) of 3,3-bis(4-fluorophenyl)propionic acid were dissolved in 200 ml of absolute ether and the solution was added dropwise to a suspension of 10.9 g (0.287 mol) of $LiAlH_4$ in 150 ml of absolute ether. When the dropwise addition had ended, the mixture was subsequently stirred for a further 30 minutes and, for hydrolysis, 175 ml of saturated sodium potassium tartrate solution and 400 ml of 10% strength $H_2SO_4$ were added dropwise in succession. After filtration, the phases were separated and the ethereal phase was washed with $NaHCO_3$ solution and NaCl solution, dried and concentrated.

Yield: 50.7 g of a yellow oil.

NMR ($CDCl_3$, 60 MHz): $\delta = 2.0-2.4$ (m, 3H), 3.48 (t, 2H), 4.01 (t, 1H) and 6.6–7.2 (m, 8H) ppm.

(e) 3,3-Bis(4-fluorophenyl)propyl bromide 50.1 g (0.202 mol) of 3,3-bis(4-fluorophenyl)propanol were dissolved in 150 ml of toluene, and a solution of 21.8 g (0.081 mol) of $PBr_3$ in 50 ml of toluene was added dropwise. The mixture was stirred at room temperature for 30 minutes and at 60° C. for 90 minutes and, for hydrolysis, was poured onto 400 ml of ice, 200 ml of ether were added, the organic phase was separated off, washed with $NaHCO_3$ solution and NaCl solution, dried and concentrated and the residue was distilled in vacuo for purification.

Yield: 32.2 g of colorless oil, boiling point 144°–162° C./0.6 mm.

(f) 1-[3,3-Bis(4-fluorophenyl)propyl]piperazine 31.1 g (0.100 mol) of 3,3-bis(4-fluorophenyl)propyl bromide, 20.6 g (0.130 mol) of ethyl piperazine-1-carboxylate, 27.6 g (0.200 mol) of powdered potassium carbonate and 4.15 g of potassium iodide were heated at the reflux temperature in 400 ml of toluene for 31 hours; the precipitate was then filtered off and the filtrate was concentrated. The material thus obtained was dissolved in 450 ml of ethanol, 450 ml of 4N KOH were added and the mixture was heated under reflux for 9 hours. After customary working up (compare Example 3d), 26.8 g of product, melting point 58°–64° C., were obtained.

EXAMPLE 5

1-[2,2-Bis(4-fluorophenyl)ethyl]piperazine (a) Bis(4-fluorophenyl)acetyl chloride 35.5 g (0.143 mol) of bis(4-fluorophenyl)acetic acid were stirred at the reflux temperature in 150 ml of thionyl chloride for 4.5 hours and the excess thionyl chloride was evaporated off in vacuo.

Yield: 38.1 g.

(b) Bis(4-fluorophenyl)acetic acid N-benzylpiperazide 25.2 g (0.143 mol) of N-benzylpiperazine and 28.9 g (0.286 mol) of triethylamine were taken in 150 ml of toluene, and a solution of 38.1 g (0.143 mol) of bis(4-fluorophenyl)acetyl chloride ... was added dropwise at 0°–5° C. in the course of 1 hour. After the mixture had been stirred at room temperature for 2 hours, the precipitate which had separated out was filtered off with suction and the filtrate was concentrated.

Yield: 58 g.

NMR ($CDCl_3$, 60 MHz), $\delta = 2.0-2.7$ (m, 4H), 3.2–3.9 (m, 6H), 5.12 (s, 1H) and 6.7–7.4 (m, 13H) ppm.

(c) 1-Benzyl-4-[2,2-bis(4-fluorophenyl)ethyl]piperazine

A solution of 58 g (0.143 mol) of bis(4-fluorophenyl) acetic acid N-benzylpiperazide in 270 ml of absolute tetrahydrofuran was slowly added dropwise to a suspension of 10.8 g (0.286 mol) of $LiAlH_4$ in 270 ml of absolute tetrahydrofuran, and the mixture was then heated under reflux for about 2 hours. For hydrolysis, 10 ml of $H_2O$ were added dropwise, followed by 50 ml of 2N NaOH and a further 10 ml of $H_2O$. The precipitate which had separated out was filtered off with suction, washed several times with tetrahydrofuran, dried and concentrated. The crude product was purified via the hydrochloride.

Yield: 41.8 g of hydrochloride, melting point 242°–246° C. (decomposition) (from isopropanol).

(d) 1-[2,2-Bis(4-fluorophenyl)ethyl]piperazine 35.1 g of 1-benzyl-4-[2,2-bis(4-fluorophenyl)ethyl]-piperazine hydrochloride were hydrogenated in 1,400 ml of methanol on 8 g of palladium-on-charcoal (10%) at room temperature for 1 hour. The catalyst was filtered off with suction, the solvent was evaporated off, the residue was dissolved in 200 ml of water, the pH was brought to 10 with 2N NaOH, the solution was extracted several times with methylene chloride and the extracts were dried and concentrated.

Yield: 17.8 g NMR ($CDCl_3$, 60 MHz), $\delta = 2.03$ (s, 1H), 2.3–3.0 (m, 10H), 4.12 (t, 1H) and 6.6–7.3 (m, 8H) ppm.

EXAMPLE 6

1-[4,5-bis(4-fluorophenyl)pentyl]piperazine (a) 4,5-Bis(4-fluorophenyl)-4-hydroxypentyl chloride A Grignard solution was prepared from 13.8 g (0.575 mol) of magnesium filings and 83.1 g (0.575 mol) of 4-fluorobenzyl chloride in 560 ml of absolute ether. This solution was added dropwise to a solution of 92 g (0.46 mol) of ω-chloro-4-fluorobutyrophenone in 300 ml of absolute ether and the mixture was heated under reflux for 2 hours. It was then poured onto 500 ml of ice, 1 liter of NH₄Cl solution was added, the mixture was extracted several times with ether and the organic phases were dried and concentrated.

Yield: 143 g of a yellow oil.

NMR (CDCl₃, 60 MHz), δ=1.2–2.3 (m, 5H), 3.0–3.6 (m, 4H) and 6.6–7.4 (m, 8H) ppm.

(b) 4,5-Bis(4-fluorophenyl)pentyl chloride 165 g (0.53 mol) of 4,5-bis(4-fluorophenyl)-4-hydroxypentyl chloride were hydrogenated in 1,650 ml of glacial acetic acid, with the addition of 16.5 g of palladium-on-charcoal (10%) and 80 ml of concentrated H₂SO₄, at room temperature for 5 hours. The catalyst was filtered off with suction, the filtrate was concentrated to about one quarter of the volume, methylene chloride and water were added, the pH was brought to 6 with concentrated NaOH and the organic phase was separated off, washed with NaHCO₃ solution and water, dried and concentrated.

Yield: 129 g

NMR (CDCl₃, 60 MHz), δ=1.3–1.9 (m, 4H), 2.8 (br, s, 2H), 3.39 (t, 2H), 3.92 (t, 1H) and 6.6–7.1 (m, 8H) ppm.

(c) 1-[4,5-Bis(4-fluorophenyl)pentyl]piperazine 50 g (0.17 mol) of 4,5-bis(4-fluorophenyl)pentyl chloride, 32.5 g (0.21 mol) of ethyl piperazine-1-carboxylate, 46.9 g (0.34 mol) of powdered potassium carbonate and 2.8 g of potassium iodide were reacted in 580 ml of methyl isobutyl ketone and the mixture was worked up, by a process analogous to that described in Example 3d).

Yield: 39.2 g.

NMR (CDCl₃, 60 MHz), δ=1.1–1.8 (m, 4H), 2.0–2.5 (m, 8H), 2.6–3.0 (m, 6H) and 6.7–7.0 (m, 8H) ppm.

EXAMPLE 7

4-[4,4-bis(4-fluorophenyl)butyl]piperidine (a) 1-Benzyl-4-[4,4-bis(4-fluorophenyl)butyl]-4-hydroxypiperidine A Grignard solution was prepared from 3.17 g (0.132 mol) of magnesium filings and 42.8 g (0.132 mol) of 4,4-bis(4-fluorophenyl)butyl bromide in 85 ml of absolute tetrahydrofuran. A solution of 25 g (0.132 mol) of distilled N-benzylpiperidone in 130 ml of absolute tetrahydrofuran was then added dropwise in the course of 30 minutes and the mixture was subsequently stirred at room temperature for 1.5 hours. The reaction mixture was poured onto 800 ml of ice, 400 ml of saturated NH₄Cl solution were added and the mixture was extracted several times with ether. The extracts were dried and concentrated.

Yield: 54.6 g.

NMR (CDCl₃, 60 MHz), δ=1.0–3.3 (m, 16H), 3.50 (s, 2H), 3.85 (t, 1H) and 6.7–7.3 (m, 13H) ppm.

(b) 1-Benzyl-4-[4,4-bis(4-fluorophenyl)butylidene]-piperidene (and isomer)

51 g (0.117 mol) of crude 1-benzyl-4-[4,4-bis(4-fluorophenyl)-butyl]-4-hydroxypiperidine were stirred in 400 ml of 85% strength phosphoric acid at 140° C. for 1.5 hours and at 160° C. for 1 hour. The reaction solution was poured onto 1 kg of ice, the pH was brought to 9, the solution was extracted with methylene chloride, the extracts were washed with water, dried and concentrated and the crude product was purified by flash column chromatography on 800 g of silica gel with (CH₂Cl₂/CH₃OH (99:1).

Yield: 18.3 g.

MS (70 eV): M⁺=417.

(c) 4-[4,4-Bis(4-fluorophenyl)butyl]piperidine 17 g (40.7 mmol) of 1-benzyl-4-[4,4-bis(4-fluorophenyl)-butylidene]piperidine were hydrogenated in 850 ml of methanol with 5 g of palladium-on-charcoal (10%) at 45° C. in a shaking vessel for 2 hours. The catalyst was filtered off with suction and the solution was concentrated.

Yield: 10.6 g.

NMR (CDCl₃, 60 MHz): δ=1.0–3.4 (m, 15H), 3.85 (t, 1H), 4.30 (s, 1H), 6.7–7.3 (m, 8H) ppm.

EXAMPLE 8

4-N-[4,4-bis(4-fluorophenyl)butyl]-N-methylaminopiperidine (a) 1-Benzyl-4-methylaminopiperidine A suspension of 20 g (0.076 mol) of 1-benzyl-4-ethoxy-carbonylaminopiperidine in 90 ml of absolute ether and 50 ml of absolute tetrahydrofuran were added to a suspension of 4.37 g (0.115 mol) of LiAlH₄ in 90 ml of absolute ether and the mixture was heated under reflux for 4.5 hours. 5 ml of H₂O, 5 ml of 2N NaOH and a further 25 ml of H₂O were added dropwise in succession, while cooling. The resulting precipitate was filtered off with suction and the filtrate was washed several times with ether, dried and concentrated.

Yield: 15.3 g.

NMR (CDCl₃, 60 MHz), δ=1.0–3.0 (m, 10H), 2.38 (s, 3H), 3.46 (s, 2H) and 7.20 (s, 5H) ppm.

(b) 1-Benzyl-4-N-[4,4-bis(4-fluorophenyl)butyl]-N-methylaminopiperidine 15.3 g (75 mmol) of 1-benzyl-4-methylaminopiperidine, 24.4 g (75 mmol) of 4,4-bis(4-flurophenyl)butyl bromide, 20.7 g (150 mmol) of powdered potassium carbonate and 1.2 g of potassium iodide were boiled under reflux in 200 ml of methyl isobutyl ketone for 63 hours. The precipitate was filtered off with suction, the filtrate was concentrated and the crude product was purified by flash column chromatography on silica gel with CH₂Cl₂/CH₃OH (99:1 to 9:1).

Yield: 25.6 g

NMR (CDCl₃, 60 MHz), δ=1.2–3.1 (m, 15H), 2.12 (s, 3H), 3.41 (s, 2H), 3.80 (t, 1H) and 6.7–7.3 (m, 13H) ppm.

(c) 4-N[4,4-Bis(4-fluorophenyl)butyl]-N-methylaminopiperidine 17.7 g (40 mmol) of 1-benzyl-4-N-[4,4-bis-(4-fluorophenyl)-butyl]-N-methylaminopiperidine were dissolved in 900 ml of 4.4% strength methanolic formic acid, the solution was added dropwise to a suspension of 17.7 g of palladium-on-charcoal (10%) in 900 ml of 4.4% strength methanolic formic acid, under an inert gas, and the mixture was heated under reflux for 90 minutes. The catalyst was filtered off with suction, the reaction solution was concentrated to dryness, the residue was taken up in a little water and the mixture was brought to pH 10 with 2N NaOH and extracted with methylene chloride. The extracts were dried and concentrated.

Yield: 10.9 g

NMR (CDCl₃, 60 MHz): δ=1.2–3.4 (m, 16H), 2.20 (s, 3H), 3.83 (t, 1H) and 6.7–7.3 (m, 8H) ppm.

EXAMPLE 9

1-[4,4-bis(4-fluorophenyl)butyl]homopiperazine 24 g (0.24 mol) of 1,4-diazacycloheptane, 7.8 g (0.024 mol) of 4,4-bis(4-fluorophenyl)butyl bromide and 0.14 g of potassium iodide were stirred in 60 ml of dimethylformamide at room temperature for 4 hours. The solvent was stripped off in vacuo, the residue was taken up in methylene chloride, the mixture was extracted by shaking with 2N HCl, the acid phase was brought to pH 11 with concentrated NaOH and extracted with methylene chloride and the extracts were dried and concentrated.

Yield: 7.15 g.

NMR (CDCl$_3$, 60 MHz): δ=1.2–3.2 (m, 16H), 3.81 (t, 1H), 4.50 (s, 1H) and 6.7–7.3 (m, 8H) ppm.

EXAMPLE 10

1-[4,4-bis(4-fluorophenyl)butyl]-4-methylaminopiperidine (a) 4-Ethoxycarbonylaminopiperidine 16 g (61 mmol) of 1-benzyl-4-ethoxycarbonylaminopiperidine were hydrogenated in 240 ml of methanol and 80 ml of 10% strength methanolic hydrochloric acid on 4 g of palladium-on-charcoal (10%) at 45° C. in a shaking vessel for 90 minutes. The catalyst was filtered off with suction, the solvent was evaporated off, the residue was dissolved in 400 ml of ethanol and the solution was neutralized with ethanolic NaOH. The NaCl which had precipitated out was filtered off and the filtrate was concentrated.

Yield: 10.5 g;
melting point 192°–194° C.

(b) 1-[4,4-Bis(4-fluorophenyl)butyl]-4-ethoxycarbonylaminopiperidine 11 g (64 mmol) of 4-ethoxycarbonylaminopiperidine, 20.5 g (64 mmol) of 4,4-bis(4-fluorophenyl)butyl bromide, 12.9 g (128 mmol) of triethylamine and 0.18 g of potassium iodide were stirred in 180 ml of absolute dimethylformamide at 80° C. for 36 hours, the mixture was diluted with about 1.5 liters of water, 100 ml of 2N NaOH were added and the mixture was extracted twice with methylene chloride.

The organic phases were dried and concentrated and the crude product was purified by flash chromatography on silica gel with CH$_2$Cl$_2$/CH$_3$OH (95:5). The product thus obtained (22.9 g) was dissolved in 350 ml of hot cyclohexane. The insoluble residue was decanted off, the solution was concentrated to half the volume, the concentrate was cooled and the precipitate was filtered off with suction.

Yield: 13.0 g;
melting point 115°–116° C.

(c) 1-[4,4-Bis(4-fluorophenyl)butyl]-4-methylaminopiperidine 13.0 g (31.3 mmol) of 1-[4,4-bis(4-fluorophenyl)butyl]-4-ethoxycarbonylaminopiperidine were dissolved in 60 ml of absolute tetrahydrofuran, the solution was added dropwise to a suspension of 1.82 g (46.9 mmol) of LiAlH$_4$ in 60 ml of absolute tetrahydrofuran and the mixture was stirred at room temperature for 1 hour and at 40° C. for 1 hour. 1.8 ml of H$_2$O, 1.8 ml of 2N NaOH and a further 9 ml of H$_2$O were added dropwise in succession, with cooling; the precipitate formed was then filtered off with suction and rinsed with a little tetrahydrofuran and the filtrate was dried and concentrated.

Yield: 9.15 g.

NMR (CDCl$_3$, 60 MHz): δ=1.0–3.0 (m, 16H), 2.42 (s, 3H), 3.86 (t, 1H) and 6.7–7.3 (m, 8H) ppm.

EXAMPLE 11

1-[4,4-bis(4-fluorophenyl)butyl]piperazine-2-carboxamide (a) 4-Tritylpiperazine-2-carboxamide 1.29 g (10 mmol) of piperazine-2-carboxamide were dissolved in 20 ml of absolute methylene chloride, 1.01 g (10 mmol) of triethylamine were added, a solution of 2.79 g (10 mmol) of triphenylmethyl chloride in 20 ml of absolute methylene chloride was added dropwise and the mixture was subsequently stirred at room temperature for 5 hours. The reaction solution was washed twice with water, dried and concentrated and the crude product was purified by flash chromatography on silica gel with CH$_2$Cl$_2$/CH$_3$OH 95:5.

Yield: 2.5 g;
melting point 229°–230° C.

(b) 1-[4,4-Bis(4-fluorophenyl)butyl]-4-tritylpiperazine-2-carboxamide 20 g (53.9 mmol) of 4-tritylpiperazine-2-carboxamide, 17.5 g (53.9 mmol) of 4,4-bis(4-fluorophenyl)butyl bromide, 14.9 g (108 mmol) of powdered potassium carbonate and 0.5 g of potassium iodide were boiled under reflux in 270 ml of methyl isobutyl ketone for 72 hours. The precipitate was filtered off and the solvent was stripped off in vacuo.

Yield: 33.1 g;
melting point 190°–191° C. (from acetone).

(c) 1-[4,4-Bis(4-fluorophenyl)butyl]-piperazine-2-carboxamide 33.1 g (53.8 mmol) of 1-[4,4-bis(4-fluorophenyl)butyl]-4-tritylpiperazine-2-carboxamide were dissolved in 180 ml of glacial acetic acid, 180 ml of water were added dropwise in the course of 15 minutes, the mixture was subsequently stirred for 90 minutes, the oily precipitate was decanted, 720 ml of H$_2$O and a Little Celite ®, a product from Johns-Mannville Corporation, New York, were added, the mixture was filtered and the filtrate was brought to pH 10 with concentrated NaOH and extracted with methylene chloride. The organic phase was dried and concentrated in vacuo.

Yield: 12.2 g

NMR (CDCl$_3$, 270 MHz): 1.3–1.6 (m, 2H), 1.85–2.4 (m 4H), 2.5–3.0 (m, 9H), 3.1–3.25 (m, 1H), 3.85 (t, 1H) 5.6–5.9 (m, 1H) and 6.8–7.2 (m, 9H) ppm.

EXAMPLE 12

4-[4,4-bis(4-fluorophenyl)butyl]piperazine-2-carboxylic acid 37.5 g (90.8 mmol) of 7-[4,4-bis(4-fluorophenyl)butyl]-hexahydro-3,3-dimethylimidazo[1,5-a]pyrazin-1(5H)-one were heated under reflux in 375 ml of 1N HCl for 2.5 hours. After cooling, the mixture was washed with methylene chloride, the aqueous phase was brought to pH 9 with concentrated NaOH and extracted twice with methylene chloride and the extracts were dried and concentrated.

Yield: 30.9 g;
melting point 184°–187° C.

EXAMPLE 13

1-[4,4-bis(4-fluorophenyl)butyl]-4-(2-chloroethyl)-piperidine (a) 1-[4,4-Bis(4-fluorophenyl)butyl]-4-(2-hydroxyethyl)-piperidine 20 g (62 mmol) of 4,4-bis(4-fluorophenyl)butyl bromide, 8.8 g (68 mmol) of 4-hydroxyethylpiperidine, 12.5 g (124 mmol) of triethylamine and 0.1 g of potassium iodide were stirred in 200 ml of absolute dimethylformamide at 80° C. for 4.5 hours. The solvent was stripped off in vacuo, the residue was taken up in methylene chloride, the mixture was extracted by shaking with 2N HCl, water and NaCl solution and the extract was dried and concentrated.

Yield: 23 g.

NMR (CDCl$_3$, 60 MHz), δ=1.2-4.0 (m, 21H) and 6.7-7.2 (m, 8H) ppm.

(b) 1-[4,4-Bis(4-fluorophenyl)butyl]-4-(2-chloroethyl)-piperidine 115 g of thionyl chloride were added dropwise to 23 g (61.6 mmol) of 1-[4,4-bis(4-fluorophenyl)butyl]-4-(2-hydroxyethyl)piperidine in 100 ml of methylene chloride, while cooling with ice, and the mixture was then heated under reflux for 5.5 hours. The solvent and excess reagent were stripped off in vacuo, the residue (the hydrochloride of the product) was crystallized by addition of 450 ml of ether and the crystals were filtered off with suction, washed several times with ether and dried in vacuo.

Yield: 22.8 g,
melting point 110°-112° C.

B. Preparation of end products of the formula I

EXAMPLE 14

5-[2-[4-[4,4-bis(4-methoxyphenyl)butyl]-piperazin-1-yl]-ethoxy]isoquinoline 3.1 g (15 mmol) of 5-(2-chloroethoxy)isoquinoline, 5.27 g (15 mmol) of 1-[4,4-bis(4-methoxyphenyl)butyl]-piperazine, 3.0 g (30 mmol) of triethylamine and 50 mg of potassium iodide were stirred in 30 ml of dimethylformamide at 80° C. for 26 hours. The reaction solution was diluted with 250 ml of water and extracted twice with methylene chloride, the extracts were evaporated in vacuo and the residue was purified by column chromatography on silica gel with CH$_2$Cl$_2$/CH$_3$OH (99:1 to 95:5).

Yield: 3.7 g.

To prepare the dimaleate, 3.7 g of the base were dissolved in 100 ml of isopropanol, a solution of 1.64 g of maleic acid in 20 ml of isopropanol was added and the precipitate which had separated out was filtered off with suction and dried.

Yield: 4.6 g;
melting point 159°-161° C. (decomposition).

EXAMPLE 15

6-[3-[4-[4,4-bis(4-fluorophenyl)butyl]piperazin-1-yl]-propoxy]-1,2,3,4-tetrahydroquinolin-2-one 2.84 g (10 mmol) of 6-(3-bromopropoxy)-1,2,3,4-tetrahydroquinolin-2-one, 3.30 g (10 mmol) of 1-[4,4-bis(4-fluorophenyl)-butyl]piperazine, 4.15 g of powdered potassium carbonate and 0.42 g of potassium iodide were boiled under reflux in 40 ml of butanone for 6 hours. The precipitate was filtered off with suction, the filtrate was concentrated, the residue was taken up in methylene chloride, the mixture was washed with 2N NaOH, dried and concentrated and the crude product was purified by column chromatography on silica gel with CH$_2$Cl$_2$/CH$_3$OH 94:6.

Yield: 3.95 g.

To prepare the dicitrate, 3.80 g of the base were dissolved in 50 ml of isopropanol, and a solution of 2.74 g of citric acid in 50 ml of isopropanol was added with heating. The precipitate which separated out in the cold was filtered off with suction and recrystallized from isopropanol.

Yield: 2.95 g, sinters from about 80° C.

EXAMPLE 16

1-[4,4-bis(4-fluorophenyl)butyl]-4-[(2-cyclohexoxy)-ethyl]piperazine 5.0 g (15.4 mmol) of 4,4-bis(4-fluorophenyl)butyl bromide, 3.26 g (15.4 mmol of 1-(2-cyclohexoxy-ethyl)-piperazine, 3.11 g (30.8 mmol) of triethylamine and 54 mg of potassium iodide were stirred at 80° C. in 35 ml of absolute dimethylformamide for 6 hours. The solvent was stripped off in vacuo, the residue was taken up in methylene chloride, the mixture was washed with 2N NaOH and water, dried and concentrated and the residue was purified by column chromatography on silica gel with CH$_2$Cl$_2$/CH$_3$OH (99:1 to 93:7).

Yield: 4.15 g of a colorless oil.

To prepare the dimaleate, 4.00 g of the base were dissolved in 50 ml of acetone, a solution of 2.04 g of maleic acid in 20 ml of acetone was added at room temperature and the resulting precipitate was filtered off with suction and dried.

Yield: 5.40 g;
melting point 189°-192° C.

EXAMPLE 17

1-[4,4-bis(4-fluorophenyl)butyl]-4-[2-]4-methylphenoxy)ethyl]piperazine

A solution of 1.18 g (11 mmol) of p-cresol in 20 ml of absolute dimethylformamide was slowly added dropwise to 0.5 g of sodium hydride dispersion (55% strength) in 8 ml of absolute dimethylformamide and the mixture was subsequently stirred at 40° C. for 1 hour. A solution of 4.85 g (12.4 mmol) of 1-[4,4-bis(4-fluorophenyl)butyl]-4-(2-chloroethyl)piperazine in 20 ml of absolute dimethylformamide was then added at room temperature and the mixture was stirred at this temperature for 48 hours. The solvent was stripped off in vacuo, the residue was dissolved in methylene chloride, the solution was washed with 2N NaOH and water, dried and concentrated and the residue was purified by column chromatography on silica gel with toluene/ethanol (99:1 to 80:20).

Yield: 3.3 g.

To prepare the dihydrochloride, 3.2 g of the base were dissolved in 15 ml of isopropanol and the pH was brought to 3 with ethanolic HCl. To bring the precipitation to completion, 30 ml of ether were slowly added and the precipitate was filtered off with suction and dried.

Yield: 3.3 g;
melting point 203°-205° C.

EXAMPLE 18

1-[4,4-bis(4-fluorophenyl)butyl]-4-[2-(1-naphthyloxy)ethyl]piperazine 2.0 g (5.1 mmol) of 1-[4,4-bis(4-fluorophenyl)butyl]-4-(2-chloroethyl)piperazine, 0.73 g (5.1 mmol) of α-naphthol, 1.41 g (10.2 mmol) of ground potassium carbonate and 50 mg of potassium iodide were heated under reflux in 10 ml of butanone for 7 hours. The solvent was evaporated off, the residue was partitioned between water and methylene chloride, the pH was brought to 8-9, the phases were separated, the organic phase was dried and concentrated and the crude product was purified by column chromatography on silica gel with $CH_2Cl_2$ and $CH_2Cl_2/CH_3OH$ 99:1.

Yield: 1.25 g.

To prepare the dimaleate, 1.1 g of the base were dissolved in 20 ml of isopropanol, and a solution of 0.51 g of maleic acid in 10 ml of isopropanol was added. The precipitate which had separated out was filtered off with suction and dried.

Yield: 1.35 g;

melting point 187°-189° C.

The compounds listed below in tabular form were obtained by the procedures described in Examples 14-18 and 96-97 using suitable starting substances and reagents.

$$R^1-O-(CH_2)_m-A-(CH_2)_n-CH\genfrac{}{}{0pt}{}{R^2}{R^3}$$

| Example | R¹ | R² | R³ | A | m | n | Salt | Melting point (°C.) |
|---|---|---|---|---|---|---|---|---|
| 19 | 5-isoquinolinyl | 4-F-phenyl | 4-F-phenyl | piperazine | 2 | 3 | dimaleate | 159–161 (decomposition) |
| 20 | " | " | " | " | 2 | 3 | dicitrate | sinters from 95 |
| 21 | " | " | " | " | 3 | 3 | dimaleate | 164–165 (decomposition) |
| 22 | " | " | " | " | 4 | 3 | " | 166–167 (decomposition) |
| 23 | " | " | " | " | 2 | 2 | " | 157–159 (decomposition) |
| 24 | phenyl | " | " | " | 2 | 3 | " | 182–185 |
| 25 | 6-isoquinolinyl | 4-F-phenyl | 4-F-phenyl | piperazine | 2 | 3 | dicitrate | sinters from 110 |
| 26 | 7-isoquinolinyl | " | " | " | 2 | 3 | dimaleate | 154–157 (decomposition) |
| 27 | 5-isoquinolinyl | " | " | homopiperazine | 2 | 3 | dimaleate | 122–126 (decomposition) |

-continued
$R^1-O-(CH_2)_m-A-(CH_2)_n-CH\genfrac{}{}{0pt}{}{R^2}{R^3}$
| Example | R¹ | R² | R³ | A | m | n | Salt | Melting point (°C.) |
|---|---|---|---|---|---|---|---|---|
| 28 | 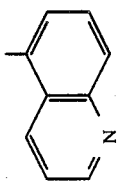 | | | 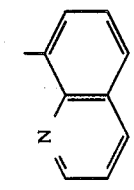 | 2 | 3 | " | 164–167 |
| 29 |  | " | " | " | 2 | 3 | " | 161–163 |
| 30 | 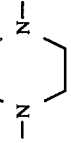 | " | " | " | 2 | 3 | trimaleate | 133–135 |
| 31 | 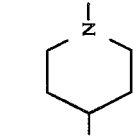 | 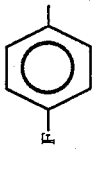 | 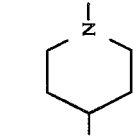 |  | 2 | 3 | dimaleate | 178–180 |
| 32 | 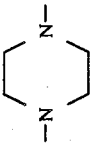 | " | " | (piperidine) | 2 | 3 | dioxalate | 100–103 (decomposition) |
| 33 | " | (phenyl) | (phenyl) | (piperazine) | 2 | 3 | dimaleate | 164 (decomposition) |

-continued $$R^1-O-(CH_2)_m-A-(CH_2)_n-CH\begin{matrix}R^2\\R^3\end{matrix}$$

| Example | R¹ | R² | R³ | A | m | n | Salt | Melting point (°C.) |
|---|---|---|---|---|---|---|---|---|
| 34 | " | 4-Cl-C₆H₄ | 4-Cl-C₆H₄ | " | 2 | 3 | " | 165 (decomposition) |
| 35 | " | 4-CF₃-C₆H₄ | 4-CF₃-C₆H₄ | " | 2 | 3 | dimaleate | 164-167 (decomposition) |
| 36 | " | 3-F-C₆H₄ | 3-F-C₆H₄ | " | 2 | 3 | " | 158-159 (decomposition) |
| 37 | 5-isoquinolinyl | 4-F-C₆H₄ | 4-F-C₆H₄ | 1-methyl-4-piperidinyl (N-CH₃ on ring N, attachment at 4) | 2 | 3 | dimaleate | 156 (decomposition) |
| 38 | " | " | " | 4-methyl-4-piperidinyl | 2 | 3 | " | 164 |
| 39 | " | " | " | piperazinyl | 2 | 4 | " | 166-167 (decomposition) |
| 40 | " | " | " | " | 2 | 1 | " | 165-166 |
| 41 | 4-O₂N-C₆H₄ | " | " | " | 2 | 3 | dihydrochloride | 154-157 |

-continued
$$R^1-O-(CH_2)_m-A-(CH_2)_n-CH\begin{matrix}R^2\\R^3\end{matrix}$$
| Example | R¹ | R² | R³ | A | m | n | Salt | Melting point (°C.) |
|---------|----|----|----|---|---|---|------|---------------------|
| 42 | 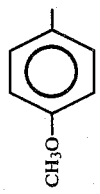 CH₃O– | " | " | " | 2 | 3 | " | 204–207 |
| 43 | 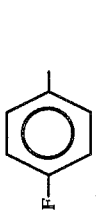 NC– | 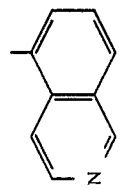 –⟨⟩–F | 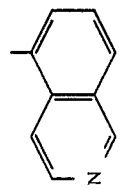 –⟨⟩–F | –N⟨ ⟩N– (piperazine) | 2 | 3 | dihydrochloride | 214–218 |
| 44 |  CH₃O–, CH₃O–, CH₃O– (trimethoxyphenyl) | " | " | " | 2 | 3 | " | 212 (decomposition) |
| 45 |  F– | " | " | " | 2 | 3 | " | 210–212 |
| 46 | 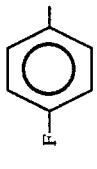 (CH₃)₃C– | " | " | " | 2 | 3 | " | 214–217 |
| 47 |  (isoquinoline) | " | " | 4-methylpiperidine (–N⟨ ⟩–CH₃) | 2 | 3 | dioxalate | 105–109 |

-continued $$R^1-O-(CH_2)_m-A-(CH_2)_n-CH\begin{matrix}R^2\\R^3\end{matrix}$$

| Example | R¹ | R² | R³ | A | m | n | Salt | Melting point (°C.) |
|---|---|---|---|---|---|---|---|---|
| 48 | isoquinolinyl | 4-F-C₆H₄- | 4-F-C₆H₄-CH₂- | piperazine | 2 | 3 | dimaleate | 152 |
| 49 | 4-H₂N-C₆H₄- | " | 4-F-C₆H₄- | " | 2 | 3 | trihydrochloride | 173–177 (decomposition) |
| 50 | 4-CF₃-C₆H₄- | " | " | " | 2 | 3 | dihydrochloride | 196–199 |
| 51 | 1-naphthyl | " | " | 2-CONH₂-piperazine | 2 | 3 | dihydrochloride | 140 (decomposition) |
| 52 | " | " | 4-F-C₆H₄-CH₂- | piperazine | 2 | 3 | dimaleate | 172–174 |
| 53 | C₆H₅- | 4-F-C₆H₄-CH₂- | piperazine | piperazine | 2 | 3 | " | 177–179 |
| 54 | cyclohexyl | 4-F-C₆H₄-CH₂- | 4-F-C₆H₄- | piperazine | 2 | 3 | dimaleate | 166–170 |

-continued
$R^1-O-(CH_2)_m-A-(CH_2)_n-CH\begin{smallmatrix}R^2\\R^3\end{smallmatrix}$
| Example | R¹ | R² | R³ | A | m | n | Salt | Melting point (°C.) |
|---------|-----|-----|-----|-----|---|---|------|---------------------|
| 55 | 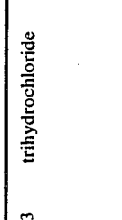 | 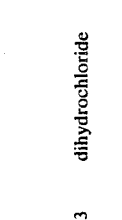 | " |  | 2 | 3 | trihydrochloride | 170–174 |
| 56 |  | " | 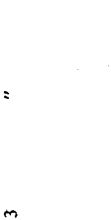 | " | 2 | 3 | dihydrochloride | 118–122 |
| 57 |  | " | " | " | 2 | 3 | " | 135–136 |
| 58 |  | " |  |  | 2 | 3 | " | 120–124 |
| 59 | 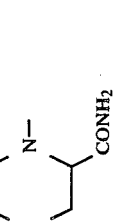 |  | 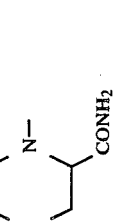 |  | 2 | 3 | Dihydrochloride | 173–178 |
| 60 | 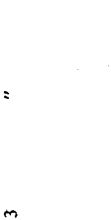 | " | " | " | 2 | 3 | " | 100–105 |

-continued $$R^1-O-(CH_2)_m-A-(CH_2)_n-CH\begin{matrix}R^2\\R^3\end{matrix}$$

| Example | R¹ | R² | R³ | A | m | n | Salt | Melting point (°C.) |
|---|---|---|---|---|---|---|---|---|
| 61 | 1-naphthyl | " | " | " | 2 | 3 | " | sinters from 110 |
| 62 | 2,6-dichlorophenyl | " | " | piperazine | 2 | 3 | " | 180–181 |
| 63 | benzoylphenyl | " | " | " | 2 | 3 | " | 130–135 |
| 64 | 3-CH₃O-phenyl | " | " | " | 2 | 3 | " | 205–207 |
| 65 | 4-CH₃O-phenyl | 4-F-phenyl | 4-F-phenyl | piperazine | 2 | 3 | Dihydrochloride | 159–161 |
| 66 | 2-COCH₃-phenyl | " | " | " | 2 | 3 | " | 173–174 |

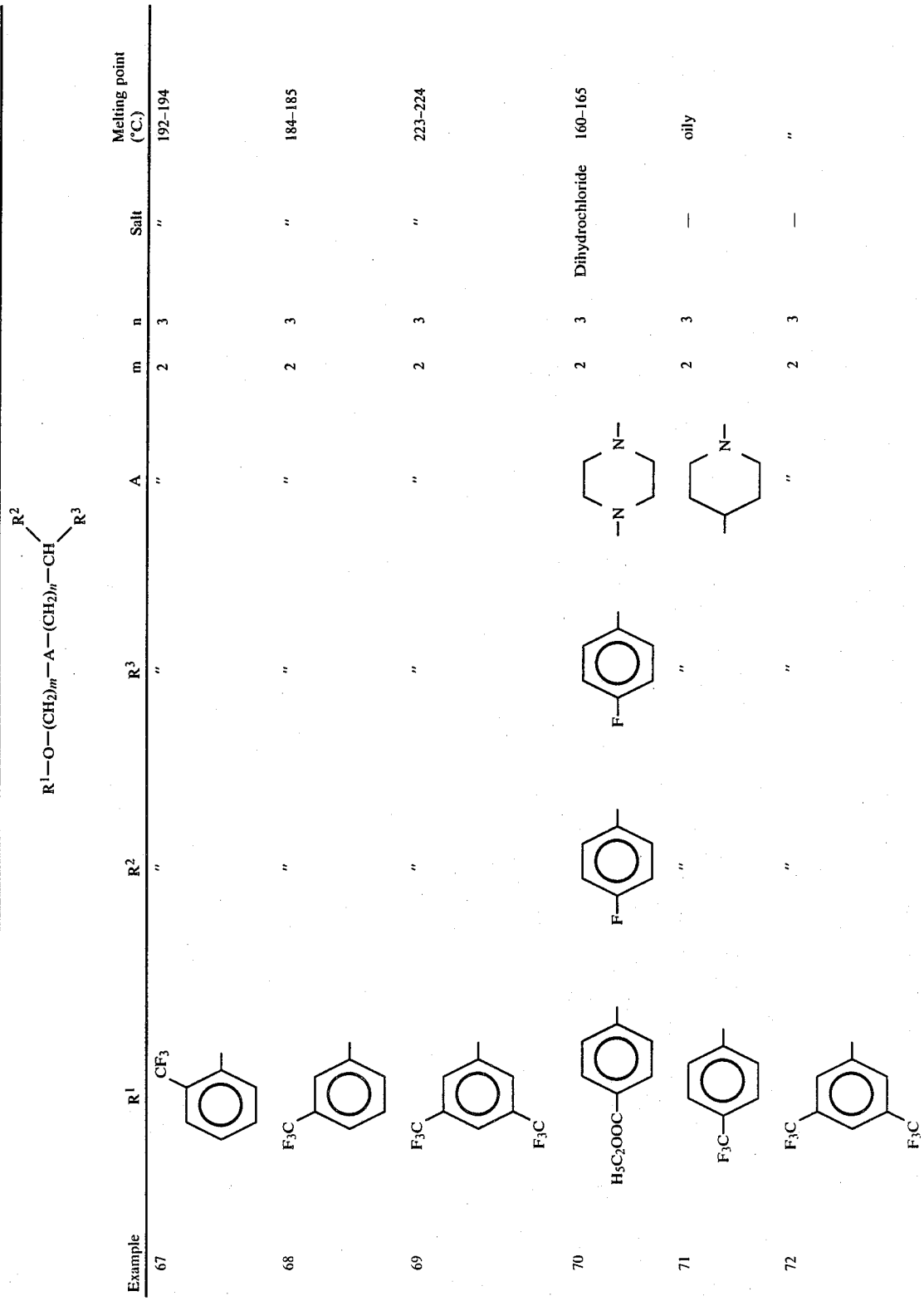

-continued $$R^1-O-(CH_2)_m-A-(CH_2)_n-CH\begin{matrix}R^2\\R^3\end{matrix}$$

| Example | R¹ | R² | R³ | A | m | n | Salt | Melting point (°C.) |
|---|---|---|---|---|---|---|---|---|
| 73 | 3-CF₃-C₆H₄ | " | " | " | 2 | 3 | — | |
| 74 | 3-F₃C-C₆H₄ | " | " | " | 2 | 3 | " | |
| 75 | 4-CH₃S-C₆H₄ | 4-F-C₆H₄ | 4-F-C₆H₄ | piperazine (−N⌒N−) | 2 | 3 | Dihydrochloride | 208–211 |
| 76 | 4-OHC-C₆H₄ | " | " | " | 2 | 3 | " | 216–220 |
| 77 | 4-CH₃CONH-C₆H₄ | " | " | " | 2 | 3 | Dioxalate | 228–235 (decomposition) |
| 78 | 3-(CH₃)₂N-C₆H₄ | " | " | " | 2 | 3 | Dimaleate | 204–207 (decomposition) |
| 79 | 4-CH₃SO₂-C₆H₄ | " | " | " | 2 | 3 | Dihydrochloride | 232–238 |

-continued $$R^1-O-(CH_2)_m-A-(CH_2)_n-CH\begin{matrix}R^2\\R^3\end{matrix}$$

| Example | R¹ | R² | R³ | A | m | n | Salt | Melting point (°C.) |
|---------|-----|-----|-----|---|---|---|------|---------------------|
| 80 | 4-H₂NCO-C₆H₄- | " | " | " | 2 | 3 | " | 214–219 (decomposition) |
| 81 | 4-Br-C₆H₄- | 4-F-C₆H₄- | 4-F-C₆H₄- | piperazine (-N⟨⟩N-) | 2 | 3 | Dihydrochloride | 215–218 |
| 82 | 4-(H₅C₂)₂NCO-C₆H₄- | " | " | " | 2 | 3 | Dimaleate | 195–198 |
| 83 | 4-(CH₃)₂NSO₂-C₆H₄- | " | " | " | 2 | 3 | Dihydrochloride | 219–222 |
| 84 | 4-H₂NSO₂-C₆H₄- | " | " | " | 2 | 3 | Dimaleate | 202–215 |
| 85 | 4-H₃CSO-C₆H₄- | " | " | " | 2 | 3 | " | 212–214 |
| 86 | 3-NO₂-5-F₃C-C₆H₃- | " | " | " | 2 | 3 | Dihydrochloride | 158–160 |

-continued $$R^1-O-(CH_2)_m-A-(CH_2)_n-CH\begin{smallmatrix}R^2\\R^3\end{smallmatrix}$$

| Example | R¹ | R² | R³ | A | m | n | Salt | Melting point (°C.) |
|---|---|---|---|---|---|---|---|---|
| 87 | 2-CF₃, 4-Cl-phenyl | 4-F-phenyl | 4-F-phenyl | piperazine | 2 | 3 | Dihydrochloride | 215–219 |
| 88 | 3-CF₃, 4-NO₂-phenyl | " | " | " | 2 | 3 | " | 198–200 |
| 89 | 3-CF₃, 4-NO₂-phenyl | " | " | " | 2 | 3 | Dimaleate | 173–175 |
| 90 | 3-CF₃-phenyl | 4-CF₃-phenyl | 4-CF₃-phenyl | " | 2 | 3 | " | 195–198 |
| 91 | 4-CF₃-phenyl | " | " | " | 2 | 3 | " | 200–202 |
| 92 | " | phenyl | phenyl | " | 2 | 3 | Dihydrochloride | 226–230 |

-continued $$R^1-O-(CH_2)_m-A-(CH_2)_n-CH\begin{matrix}R^2\\R^3\end{matrix}$$

| Example | R¹ | R² | R³ | A | m | n | Salt | Melting point (°C.) |
|---|---|---|---|---|---|---|---|---|
| 93 | 3-F₃C-C₆H₄- | C₆H₅- | C₆H₅- | piperazine (−N⌒N−) | 2 | 3 | Dihydrochloride | 218–220 |
| 94 | (CH₃)₂C=CH−CH₂− | 4-F-C₆H₄- | 4-F-C₆H₄- | " | 2 | 3 | " | 183–185 |
| 95 | cyclohex-2-enyl | " | " | " | 2 | 3 | " | 163–164 |

EXAMPLE 96

1-[4,4-Bis-(4-fluorophenyl)butyl]-4-[2-(2,4-dinitrophenoxy)ethyl]piperazine 3.36 g (9.0 mmol) of 1-[4,4-bis-(4-fluorophenyl)-butyl]-4-(2-hydroxyethyl)piperazine, dissolved in 12 ml of absolute dimethylformamide, were added dropwise to a suspension of 0.432 g (10 mmol) of a 55% sodium hydride dispersion in 10 ml of absolute dimethylformamide in the course of 5 minutes and the mixture was then subsequently stirred at 20° C. and then at 40° C., for in each case one hour. A solution of 1.82 g (9.0 mmol) of 2,4-dinitrochlorobenzene in 10 ml of absolute dimethylformamide was then added dropwise, while cooling with ice, such that the temperature did not rise above 10° C. The mixture was then stirred at room temperature for a further 3 hours, poured onto 300 ml of water and extracted twice by shaking with methylene chloride. The organic extracts were combined, dried and concentrated under an oil pump vacuum at 40° C., and the residue was purified by column chromatography on silica gel with $CH_2Cl_2/CH_3OH$ (99:1 to 97.5:2.5).

Yield: 2.50 g of a yellowish oil.

To prepare the dihydrochloride, 2.40 g of the base were dissolved in 50 ml of hot isopropanol and the pH was brought to 2 by addition of ethereal HCl. The precipitate which occurred on cooling was completed by addition of 100 ml of ether, filtered off with suction and dried.

Yield: 2.40 g,
melting point 183°–185° C.

EXAMPLE 97

1-[4,4-bis-(4-fluorophenyl)butyl]-4-[2-(2-methyl-4-nitrophenoxy)ethyl]piperazine 3.36 g (9.0 mmol) of 1-[4,4-bis-(4-fluorophenyl)-butyl]-4-(2-hydroxyethyl)piperazine, dissolved in 15 ml of absolute dimethylformamide, were added dropwise to a suspension of 0.43 g (10 mmol) of a 55% strength sodium hydride dispersion in 10 ml of absolute dimethylformamide and the mixture was stirred at 60° C. for 90 minutes. A solution of 1.28 g (0.90 mol) of 2-fluoro-5-nitrotoluene in 5 ml of absolute dimethylformamide was then added, while cooling with ice, and the mixture was subsequently stirred at room temperature for 3 hours. The reaction solution was poured onto water and extracted twice with methylene chloride, the combined organic phases were dried and concentrated and the residue was purified by column chromatography on silica gel with toluene/ethanol (99:1 to 95:5).

Yield: 2.80 g of a colorless oil.

To prepare the dihydrochloride, 2.70 g of the base were dissolved in 30 ml of ethyl acetate and ethereal HCl was added. The precipitate which had separated out was filtered off with suction and dried.

Yield: 2.75 g;
melting point 202°–204° C.

We claim:

1. A compound of the formula I

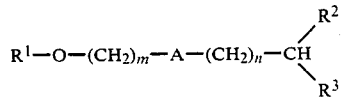

(I)

in which:

$R^1$ is $(C_3-C_8)$-cycloalkyl, straight-chain or branched $(C_2-C_6)$-alkenyl, $(C_5-C_8)$-cycloalkenyl, or is

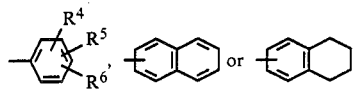

in which $R^4$, $R^5$ and $R^6$ are identical or different and independently of one another are hydrogen, $(C_1-C_6)$-alkyl, $(C_3-C_8)$-cycloalkyl, hydroxyl, $(C_1-C_4)$-alkoxy, $(C_1-C_4)$-alkylthio, F, Cl, Br, I, nitro, cyano, trifluoromethyl, formyl, carboxyl, $(C_1-C_6)$-alkoxycarbonyl, $(C_1-C_6)$-acyl, carbamoyl, N-mono- or N,N-di-$(C_1-C_6)$-alkylcarbamoyl, sulfo, $(C_1-C_6)$-alkoxysulfonyl, sulfamoyl, N-mono- or N,N,-di-$(C_1-C_6)$-alkylsulfamoyl, $(C_1-C_6)$-alkylsulfinyl, $(C_1-C_6)$-alkylsulfonyl or amino, unsubstituted or substituted by one or two identical or different $(C_1-C_6)$-alkyl, $(C_1-C_6)$-acyl or phenyl groups, $R^2$ and $R^3$ are identical or different and independently of one another are phenyl or phenyl-$(C_1-C_4)$-alkyl, the phenyl ring in each case being unsubstituted or substituted by one, two or three substituents selected from the group consisting of $(C_1-C_4)$-alkyl, $(C_1-C_4)$-alkoxy, F, Cl, Br, I, cyano, nitro and trifluoromethyl, and A is an amine of the formula:

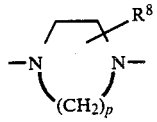

in which $R^8$ is hydrogen, $(C_1-C_6)$-alkyl, formyl, $(C_1-C_6)$-acyl, carboxyl, $(C_1-C_6)$-alkoxycarbonyl, carbamoyl or N-mono-or N,N-di-$(C_1-C_6)$-alkylcarbamoyl, and p is 2, m is 2, 3 or 4 and n is 1, 2, 3 or 4 or a salt of a compound of the formula I with a physiologically acceptable acid.

2. A compound of the formula I as claimed in claim 1, in which at least one of the radicals and indices has the following meaning:

$R^1$ is $(C_3-C_8)$-cycloalkyl, or is

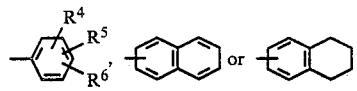

in which $R^4$ and $R^5$ are identical or different and independently of one another are hydrogen, $(C_1-C_6)$-alkyl, $(C_1-C_4)$-alkoxy, F, Cl, Br, I, nitro, cyano, trifluoromethyl, formyl, carboxyl, $(C_1-C_6)$-alkoxycarbonyl, $(C_1-C_6)$-acyl, carbamoyl, N-mono- or N,N-di-$(C_1-C_6)$-alkylcarbamoyl, sulfo, $(C_1-C_6)$-alkylsulfonyl, sulfamoyl, N-mono- or N,N-di-$(C_1-C_6)$-alkylsulfamoyl, $(C_1-C_6)$-alkylsulfinyl or $((C_1-C_6)$-alkylsulfonyl, $R^6$ is hydrogen and $R^2$ and $R^3$ are identical or different and independently of one another are phenyl, which is unsubstituted or substituted by one, two or three substituents from the group consisting of methyl, ethyl, methoxy, ethoxy, F, Cl, Br, I, cyano, nitro and trifluoromethyl, A is an amine of the formula:

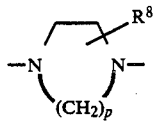

in which
$R^8$ is hydrogen, carboxyl or carbamoyl, and
p is 2,
m is 2, 3 or 4 and
n is 1, 2, 3 or 4 or a salt of a compound of the formula I with a physiologically acceptable acid.

3. A compound of the formula I as claimed in claim 1, in which at least one of the substituents and indices has the following meaning:
$R^1$ is $(C_5-C_7)$-cycloalkyl, or is

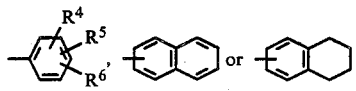

in which
$R^4$ is hydrogen, methyl, ethyl, propyl, isopropyl, n-butyl, s-butyl, isobutyl, tert. butyl, methoxy, ethoxy, fluorine, chlorine, bromine, nitro, cyano or trifluoromethyl, and
$R^5$ and $R^6$ each is hydrogen,
$R^2$ and $R^3$ are identical or different and independently of one another are phenyl, which is unsubstituted or substituted by one, or two or three substituents from the group consisting of methyl, fluorine, chlorine, bromine, cyano, nitro and trifluoromethyl,
A is an amine of the formula:

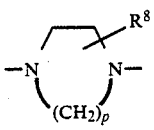

in which
$R^8$ is hydrogen, carboxyl or carbomoyl, and
p is 2,
m is 2, 3 or 4 and
n is 2, 3 or 4, or a salt of a compound of the formula I with a physiologically acceptable acid.

4. A compound of the formula I as claimed in claim 1, in which at least one of the substituents or indicies has the following meaning:
$R^1$ is cyclohexyl, or is phenyl which is unsubstituted or substituted by methyl, tert. butyl, methoxy, fluorine, nitro, cyano or trifluoromethyl,
$R^2$ and $R^3$ are identical or different and independently of one another are phenyl, which is unsubstituted or substituted by fluorine or trifluoromethyl,
A is an amine of the formula:

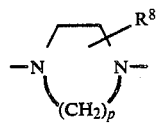

in which
$R^8$ is hydrogen, and
p is 2,
m is 2 and
n is 3, or a salt of a compound of the formula I with a physiologically acceptable acid.

5. A pharmaceutical composition comprising an amount effective for use as a pharmaceutical in the therapy of a mammal of a compound of the formula I as claimed in claim 1 or a salt of said compound with a physiologically acceptable acid, together with a pharmaceutically acceptable carrier.

* * * * *